(12) United States Patent
Nose et al.

(10) Patent No.: US 8,680,477 B2
(45) Date of Patent: Mar. 25, 2014

(54) NON-DESTRUCTIVE INSPECTION METHOD AND DEVICE

(75) Inventors: Hiroyuki Nose, Tokyo (JP); Hajime Kuwabara, Tokyo (JP); Tetsuya Kobayashi, Tokyo (JP)

(73) Assignee: IHI Corporation, Tokyo (JP)

( * ) Notice: Subject to any disclaimer, the term of this patent is extended or adjusted under 35 U.S.C. 154(b) by 153 days.

(21) Appl. No.: 13/501,589

(22) PCT Filed: Oct. 8, 2010

(86) PCT No.: PCT/JP2010/067743
§ 371 (c)(1),
(2), (4) Date: Apr. 12, 2012

(87) PCT Pub. No.: WO2011/046078
PCT Pub. Date: Apr. 21, 2011

(65) Prior Publication Data
US 2012/0199754 A1    Aug. 9, 2012

(30) Foreign Application Priority Data
Oct. 15, 2009    (JP) .................. 2009-238332

(51) Int. Cl.
*G01T 1/16*    (2006.01)
(52) U.S. Cl.
USPC .................. 250/393; 250/390.01; 250/269.6
(58) Field of Classification Search
USPC .......................................................... 250/393
See application file for complete search history.

(56) References Cited

U.S. PATENT DOCUMENTS 5,080,856 A * 1/1992 Grenier et al. ................ 376/159
5,098,640 A   3/1992 Gozani et al.
5,410,575 A * 4/1995 Uhm ............................. 376/159
5,412,206 A   5/1995 Seidel et al.
5,539,788 A   7/1996 Ruddy et al.
8,080,808 B2 * 12/2011 Norris ...................... 250/390.04

(Continued)

FOREIGN PATENT DOCUMENTS

JP    7 294652    11/1995
JP    7 301610    11/1995

(Continued)

OTHER PUBLICATIONS

U.S. Appl. No. 13/501,468, filed Apr. 12, 2012, Nose, et al.
Japanese Office Action issued May 7, 2013 in Patent Application No. 2009-238332 with English Translation.
Kodai Yamada et al., "Study on Non-Destructive Measurement of Chrolide Ion in Concrete Distribution by Prompt Gamma Ray Analysis", Concrete Engineering Annual Papers, vol. 31, No. 1, Jul. 2009, pp. 1981-1986.
Matsue, H., "Prompt Gamma Ray Analysis Method Using Neutron Resonance Absorption," Database of Radiation Applications, Radiation Technique, Paper 47, Total 4 Pages, (Feb. 21, 2003) (with partial English translation).
International Search Report Issued Nov. 16, 2010 in PCT/JP10/67743 Filed Oct. 8, 2010.

*Primary Examiner* — Marcus Taningco
(74) *Attorney, Agent, or Firm* — Oblon, Spivak, McClelland, Maier & Neustadt, L.L.P.

(57) ABSTRACT

A method of non-destructive inspection of a subject body including one or more elements comprises irradiating the subject body with a neutron ray along an axis line passing through a reference point; synchronously detecting gamma rays from directions inclined at equal angles to the axis line at a plurality of measurement points disposed to have equivalent intervals radially from the axis line, respectively; measuring the detected gamma rays in a plurality of energy ranges; determining whether measured values in the respective energy ranges are beyond thresholds; determining energy ranges where all the measured values are beyond the thresholds; analyzing a type of an element from the determined energy ranges; and detecting a location of the analyzed type of the element in the subject body on the basis of the reference point, the respective measurement points, a relative position relative to a surface of the subject body, and the directions.

6 Claims, 3 Drawing Sheets

(56) References Cited

U.S. PATENT DOCUMENTS

| | | | |
|---|---|---|---|
| 2003/0147484 A1* | 8/2003 | Olshansky et al. | 376/157 |
| 2006/0192095 A1* | 8/2006 | Stoller et al. | 250/261 |
| 2007/0069145 A1 | 3/2007 | Leonhardt | |
| 2010/0065727 A1 | 3/2010 | Choi | |

FOREIGN PATENT DOCUMENTS

| | | |
|---|---|---|
| JP | 3144641 | 3/2001 |
| JP | 2004 125639 | 4/2004 |
| WO | 2008 012360 | 1/2008 |

\* cited by examiner

NON-DESTRUCTIVE INSPECTION METHOD AND DEVICE

TECHNICAL FIELD

The present invention relates to a method and a device of non-destructive inspection by which a state of a subject body is inspected without destroying the subject body.

BACKGROUND ART

As inspection of states (corrosion, cracks, cavity formation, or such) of structures or components, a visual inspection, a hammering test, an ultrasonic inspection (echo inspection) and such have been applied so far. The visual inspection and the hammering test are, however, likely to cause variations in inspection results depending on skill levels of inspectors, and inherently have limited inspection accuracy. These inspection methods are, in addition, applicable only to parts where workers can observe or hammer. While the ultrasonic inspection may not cause issues led from artificial inspection as discussed above, there is a difficulty in determination of locations.

There are proposed some inspection methods having accuracy, which utilize radiation. The non-patent literature as described below discloses an analysis method using a prompt gamma ray. The term "prompt gamma ray" generally means a ray emitted by a nuclear reaction within a very short time, but is herein particularly defined as a gamma ray emitted just after trapping of an epithermal neutron by resonance absorption.

CITATION LIST

Non Patent Literature

[NPL 1]: PROMPT GAMMA RAY ANALYSIS METHOD USING NEUTRON RESONANCE ABSORPTION (Database of Radiation Applications, Radiation Technique, 047 Paper, http://www.rada.or.jp/database/home4/normal/ht-docs/member/synopsis/040275.html)

DISCLOSURE OF INVENTION

According to the aforementioned analysis method using a prompt gamma ray, relatively small subject bodies can be inspected without destroying them. In cases where subject bodies are relatively large, however, the method requires to cut out some test pieces from the subject bodies. Thus the analysis using a prompt gamma ray has difficulty in execution as a non-destructive inspection method. Further, while a prompt gamma ray is inherently available for elementary analysis as it has an energy specific to an element, a problem of accuracy may arise because a gamma ray of high energy resulted from Compton scattering and such is likely to get mixed in the prompt gamma ray.

The present invention has been achieved in view of the aforementioned issues and is intended to provide a non-destructive inspection method without constraints about a shape of a subject body and locations of contained substances, and a non-destructive inspection device preferably applicable to the method, for the purpose of accurate inspection of states of the subject body.

According to a first aspect of the present invention, a method of non-destructive inspection of a subject body including one or more elements is comprised of the steps of irradiating the subject body with a neutron ray along an axis line passing through a reference point; synchronously detecting gamma rays from directions inclined at equal angles to the axis line at a plurality of measurement points disposed to have equivalent intervals radially from the axis line, respectively; measuring the detected gamma rays in a plurality of energy ranges; determining whether measured values in the respective energy ranges are beyond thresholds; determining energy ranges where all the measured values are beyond the thresholds; analyzing a type of an element from the determined energy ranges; and detecting a location of the analyzed type of the element in the subject body on the basis of the reference point, the respective measurement points, a relative position relative to a surface of the subject body, and the directions.

According to a second aspect of the present invention, a device of non-destructive inspection of a subject body including one or more elements is comprised of a neutron ray source having a reference point and disposed so as to irradiate the neutron ray along an axis line passing through the reference point; a plurality of gamma ray monitors configured to respectively detect gamma rays from directions inclined at equal angles to the axis line, the gamma ray monitors being disposed at a plurality of measurement points having equivalent intervals radially from the axis line; a plurality of wave height analyzers configured to respectively measure the detected gamma rays in a plurality of energy ranges respectively, the wave height analyzers being respectively electrically connected with the gamma ray monitors; a controller configured to determine whether measured values in each energy ranges are beyond thresholds or not, determine an energy range where all of the measured values are beyond the thresholds, analyze a type of an element from the determined energy range, and detect a location of the analyzed type of the element in the subject body on the basis of the reference point, the respective measurement points, a relative position relative to a surface of the subject body, and the directions.

BEST MODE FOR CARRYING OUT THE INVENTION

Certain embodiments will be described hereinafter with reference to the appended drawings.

Figure 1:
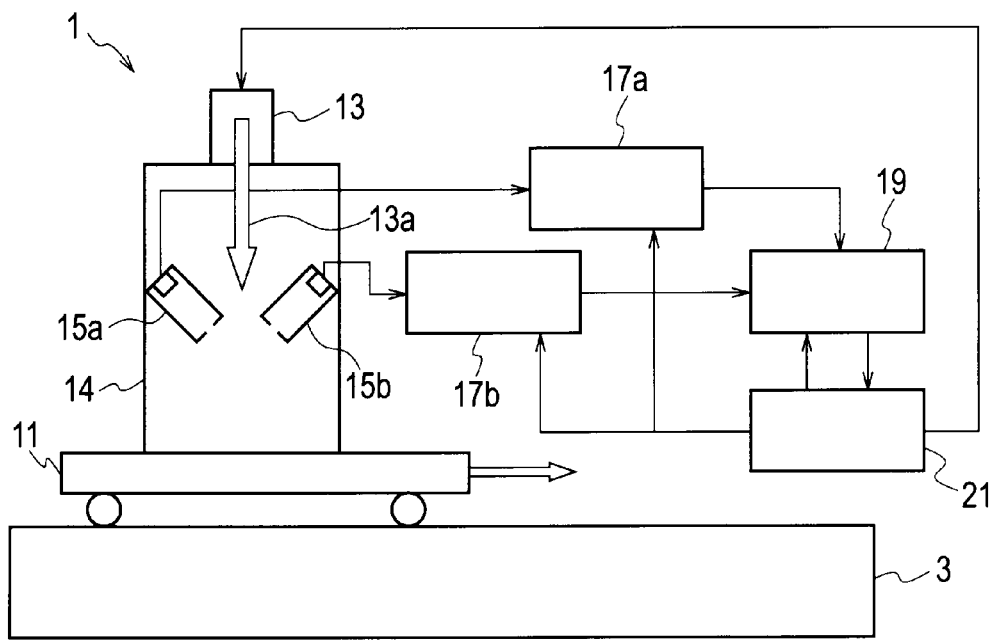
FIG. 1 is an outlined structural drawing of a non-destructive inspection device related to an embodiment of the present invention, in which a non-destructive inspection method according to the present invention.

FIG. 1 is an outlined structural drawing illustrating a non-destructive inspection device in accordance with an embodiment of the present invention to which a non-destructive inspection method according to the present invention.

The non-destructive inspection device 1 utilizes a phenomenon that an atomic nucleus capturing a neutron emits a prompt gamma ray, and inspects a state of a subject body by detecting a prompt gamma ray from the subject body which is irradiated with a neutron. Descriptions will be given hereinafter in regard to an example in which reinforced concrete 3 constituting a bridge or such is a subject body and inspection is carried out in order to know a state of corrosion by a chloride attack. The subject of inspection is a distribution of a reinforcing bar in the reinforced concrete 3 and a distribution of chlorine (or chloride ion) that causes the chloride attack.

The non-destructive inspection device 1 of the present embodiment is comprised of a mobile pedestal 11 movable on the reinforced concrete 3, a neutron ray source 13 for outputting a neutron ray, and a gamma ray detector 15 for detecting a prompt gamma ray from the reinforced concrete 3. The neutron ray source 13, the resonant neutron detector 14, and the gamma ray detector 15 are set up on the mobile pedestal 11.

The non-destructive inspection device 1 of the present embodiment is comprised of a wave height analyzers 17a, 17b, a synchronous measurement device 19 connected with both the wave height analyzers 17a,17b, and a controller 21 for controlling them. The wave height analyzers 17a,17b respectively measure the prompt gamma ray in accordance with the outputs from the gamma ray detectors 15a,15b. The wave height analyzers 17a, 17b decompose intensities of gamma rays into spectra about energies and are capable of measuring the gamma ray intensities in respective energy regions. The synchronous measurement device 19 is capable of setting thresholds in regard to the respective outputs of the wave height analyzers 17a, 17b, and is configured to output a detection signal to the controller 21 when a signal beyond a threshold is input.

To the mobile pedestal 11 applicable is any cart movable on the reinforced concrete 3. Alternatively a self-propelled cart having a drive source may be applied thereto. Meanwhile it is preferable that a position (position on the reinforced concrete 3 where irradiated with a neutron ray by the neutron ray source 13) of the mobile pedestal 11 on the reinforced concrete 3 is continuously grasped by the controller 21, even whether the mobile pedestal 11 is self-propelled or driven. One of axles of the mobile pedestal 11 may be, for example, comprised of a revolution counter to allow the controller 21 to integrate the output of the revolution counter, thereby grasping the position. Alternatively the mobile pedestal 11 may be comprised of a distance meter, an acceleration meter, or a position sensor instead of the revolution counter.

Figure 2:
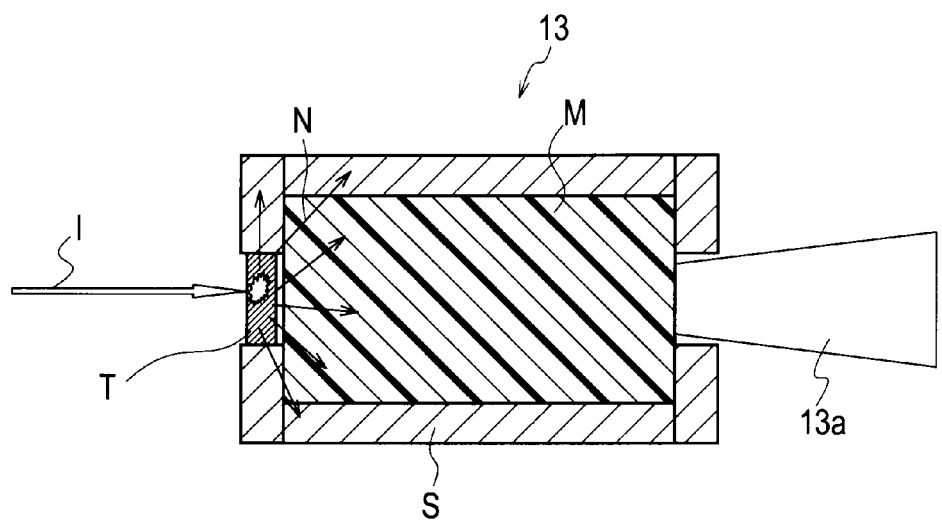
FIG. 2 is an explanatory drawing depicting a principle of generating a neutron ray at a neutron ray source of FIG. 1.

To the neutron ray source 13 applicable is any one known in the art. The neutron ray source 13 as shown in FIG. 2 is, for example, comprised of a target T to be irradiated with ions I, a moderating material M for moderating or slowing down fast neutrons N, and a protective wall S for protecting the fast neutrons N and the moderating material M from the exterior. The target T includes materials such as Be or $^2$H so as to effectively generate neutrons from ions I such as H, $^2$H or $^4$He emitted from an external ion generator. The moderating material M is formed of any proper material, such as polyethylene, heavy water, or light water for example, to moderate or slow down the fast neutrons N generated in the target T. The fast neutrons N are converted into a neutron ray 13a having a continuous spectrum including thermal neutrons (0.5 eV or less) and epithermal neutrons (0.5-$10^3$ eV) by the moderating material M. The proper moderator protective wall S encapsulates the moderating material M and also prevents the fast neutrons N from leaking out. Further one end of the protective wall S (normally the opposite side to the target) opens to radiate the neutron ray 13a therethrough to the exterior. The neutron ray source 13 is set up on an upper portion of a protective body 14 of a chamber-like form set up on the mobile pedestal 11. The neutron ray 13a output from the neutron ray source 13 (see FIG. 1) passes through the interior of the protective body 14 and the mobile pedestal 11 and is emitted onto the reinforced concrete 3 in a direction of a normal line relative to its surface.

Figure 3:
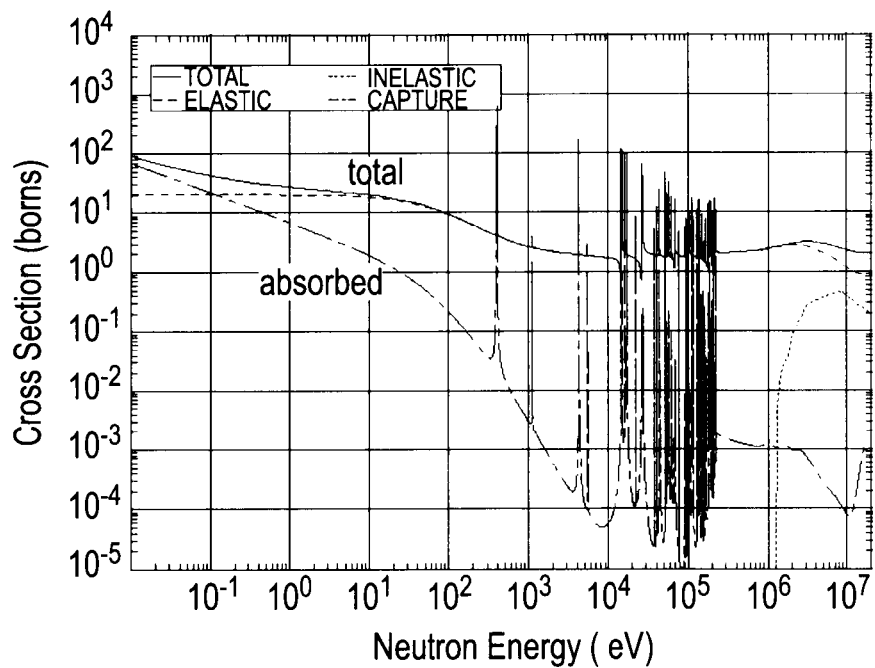
FIG. 3 is a graph depicting a relation between a neutron energy and a capture cross-section in regard to chlorine 35.
Figure 4:
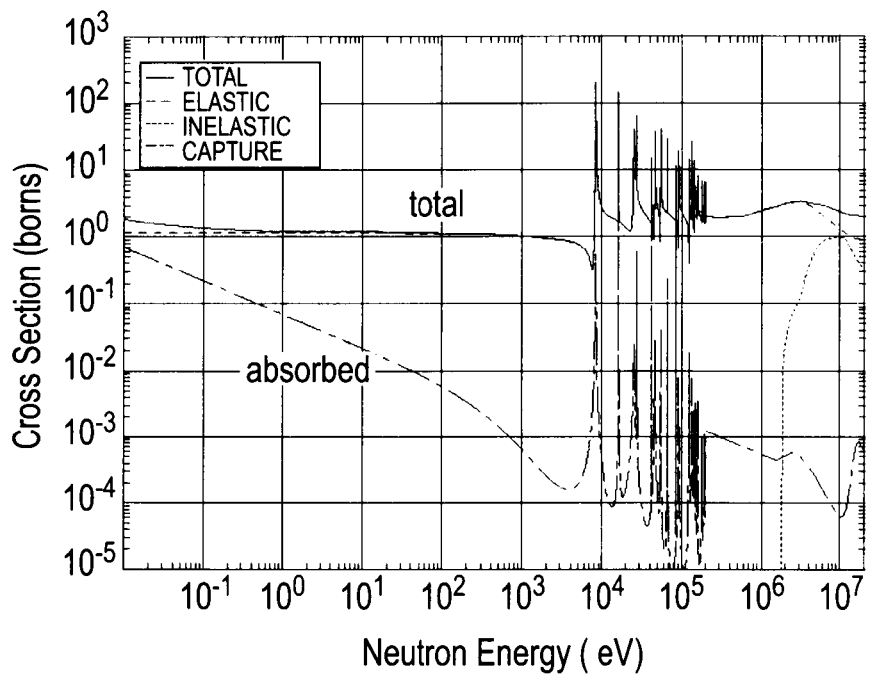
FIG. 4 is a graph depicting a relation between a neutron energy and a capture cross-section in regard to chlorine 37.

When an atomic nucleus is irradiated with the neutron ray 13a including epithermal neutrons, resonant absorption of neutrons having energies specific to the atomic nucleus occurs. A neutron subject to resonant absorption into an atomic nucleus is referred to as a resonant neutron. The graphs of FIG. 3 and FIG. 4 show relations between energies of emitted neutrons and capture cross sections in regard to chlorine 35 and chlorine 37, respectively. As will be understood if FIG. 3 (chlorine 35) is compared with FIG. 4 (chlorine 37), acknowledged are sharp peaks compared with adjacent energy regions in a capture cross section curve, which are at a specific neutron energy region around $10^2$-$10^3$ eV and corresponding to epithermal neutrons. More specifically, there are neutrons specifically subject to resonant absorption into chlorine 35 (these are distinct from those of chlorine 37), which are referred to as "resonant neutrons" hereinafter. Use of the resonant neutrons enables discrimination of chlorine 35 from chlorine 37 by determining whether the subject absorbs the resonant neutrons or not. Throughout the present specification and the appended claims, the term "resonant neutron" is defined and used as a meaning of "a neutron among neutrons included in a neutron ray with a continuous spectrum, which has an energy corresponding to a resonant level specific to an element, thereby being resonantly absorbed into the element".

An atomic nucleus capturing a resonant neutron by resonant absorption emits a prompt gamma ray. The energy of the prompt gamma ray differs in accordance with the neutron energy of the resonant neutron captured by the atomic nucleus. Therefore an energy of a prompt gamma ray emitted by a nucleus is specific to the nucleus. By utilizing this principle, the non-destructive inspection device 1 of the present embodiment analyzes a distribution of elements (in particular, iron used as a reinforcing bar, and chlorine as chloride ion) contained in the reinforced concrete 3. For this purpose, in the non-destructive inspection device 1, a neutron ray 13a as epithermal neutrons emitted from the neutron ray source 13 is emitted onto the reinforced concrete 3 and a prompt gamma ray emitted from (particular elements contained in) the reinforced concrete is detected by the gamma ray detectors 15a, 15b.

Figure 5:
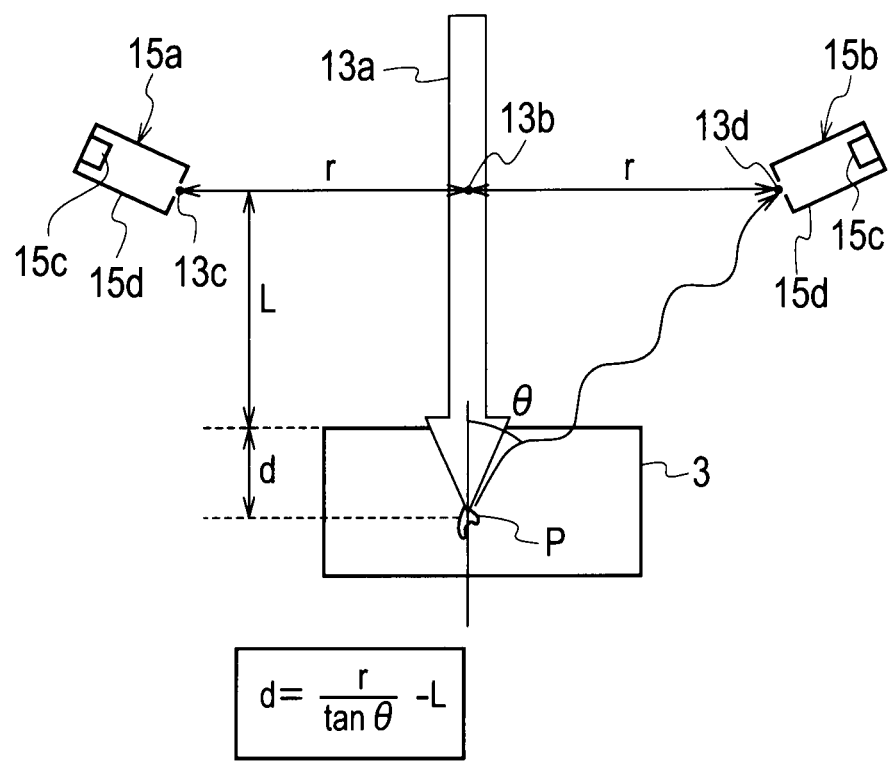
FIG. 5 is an explanatory drawing depicting a principle of location analysis of chlorine by means of the non-destructive inspection device of FIG. 1.

The gamma ray detectors 15a, 15b are, as shown in FIG. 1, housed in the protective body 14 on the mobile pedestal 11. The respective gamma ray detectors 15a, 15b are, as shown in FIG. 5, disposed at reference points 13c, 13d respectively having equivalent intervals from a reference point 13b on an irradiation axis line of the neutron ray 13a from the neutron ray source 13 toward radial directions perpendicular to the irradiation axis line. This reference point 13b is set at a point distant away from a surface of the reinforced concrete 3 by a distance L.

Each gamma ray detector 15a, 15b is comprised of a gamma ray sensor 15c and a collimator 15d covering the gamma ray sensor 15c.

To the gamma ray sensor 15c applicable is any gamma ray sensor known in the art. A scintillation detector comprised of a scintillator that receives a gamma ray to emit fluorescent light, and a photomultiplier tube or a photodiode that measures intensity of this fluorescent light is applicable. Alternatively a known semiconductor detector can be used.

The collimator 15*d* is configured to limit incident directions of a gamma ray detectable by the gamma ray sensor 15*c*. In the present embodiment, the collimator 15*d* of any of the gamma ray detector 15*a*, 15*b* collimate a prompt gamma ray from a reinforced concrete 3 to make a gamma ray in a direction inclined at an angle θ to an irradiation axis line of the neutron ray 13*a* reach the gamma ray sensor 15*c*. Thus the gamma ray sensor 15*c* detects only a gamma ray in the direction inclined at the angle θ to the irradiation axis line of the neutron ray 13*a*.

The gamma ray detectors 15*a*, 15*b* constituted in a way described above detect a prompt gamma ray that a specific element contained in the reinforced concrete 3 irradiated with the neutron ray 13*a* captures a resonant neutron to emit. FIG. 5 shows an example in which the non-destructive inspection device 1 detects chlorides in a case where the chlorides exist at a particular location P in the reinforced concrete 3.

As the gamma ray detectors 15*a*, 15*b* have a positional relation as described above, the respective gamma ray detectors 15*a*, 15*b* receive a prompt gamma ray from a particular location P when they are directed in an angle θ corresponding to the particular location P. Thus the controller 21 calculates a position of the particular location P by a simple math formula if the prompt gamma ray is detected. The math formula then used can be represented by $d=(r/\tan θ)-L$, given that a subject element locates at a position inner by a depth d from a surface of the reinforced concrete 3.

The respective wave height analyzers 17*a*, 17*b*, when being triggered by the controller 21 in synchronization with output of the neutron ray 13*a* from the neutron ray source 13, decompose gamma rays respectively detected by the correspondent gamma ray detectors 15*a*, 15*b* into components on the basis of a plurality of energy ranges and then measures these intensities in the respective energy ranges.

The synchronous measurement device 19, when being triggered by the controller 21 in synchronization with output of the neutron ray 13*a* from the neutron ray source 13, obtains the intensities measured by the respective wave height analyzer 17*a*, 17*b* in the respective energy ranges. Then the synchronous measurement device 19 compares the respective intensities obtained from the respective wave height analyzers 17*a*, 17*b* with the aforementioned thresholds. The synchronous measurement device 19 determines whether any of the gamma ray intensities detected by the respective gamma ray detectors 15*a*, 15*b* is higher or not than the thresholds in regard to the respective energy ranges. These predetermined thresholds are set by the controller 21 on each gamma ray energy range. Further the thresholds of each energy range are common to the wave height analyzers 17*a*, 17*b*.

The synchronous measurement device 19 as described above outputs a determination signal indicating an energy range where an intensity of a gamma ray simultaneously detected by the gamma ray detectors 15*a*, 15*b*, which is decomposed by the wave height analyzers 17*a*, 17*b*, is higher than predetermined thresholds at the energy range in question.

The controller 21 analyze and identifies an element existing in the reinforced concrete 3 irradiated with the neutron ray 13*a* from the neutron ray source 13 on the basis of the determination signal output by the synchronous measurement device 19, and further uses the math formula as described above to calculate a location of the identified element in the reinforced concrete 3 (a depth d from a surface of the reinforced concrete 3) on the basis of the positional relation of the gamma ray detectors 15*a*, 15*b*.

In inspection of the reinforced concrete 3 with using the non-destructive

In inspection of the reinforced concrete 3 with using the non-destructive inspection device 1 of the present embodiment as constituted as above, a location of the mobile pedestal 11 on the reinforced concrete 3, in other words an irradiated location of the reinforced concrete 3 with the neutron ray 13*a*, is changed throughout the whole surface of the reinforced concrete 3, like a matrix for example, in each cycle.

Then at each location irradiated with the neutron ray 13*a*, the following steps (1) through (4), more specifically:

(1) the step of radiating a neutron ray 13*a* from a neutron ray source 13 toward a reinforced concrete 3 to cause a nucleus of an element contained in the reinforced concrete 3, which captures a neutron in the neutron ray 13*a*, to emit a prompt gamma ray;

(2) the step of detecting a gamma ray from a direction inclined at an angle θ to an irradiation axis line of the neutron ray 13*a* by the gamma ray detectors 15*a*, 15*b* at reference points 13*c*, 13*d* respectively having equivalent intervals from a reference point 13*b* on an irradiation axis line of the neutron ray 13*a* from the neutron ray source 13 toward radial directions perpendicular to the irradiation axis line;

(3) the step of decomposing intensities of a gamma ray detected by the gamma ray detectors 15*a*, 15*b* into components in respective ranges; and (4) the step in that the controller 21, in a case where intensities of a gamma ray simultaneously detected by the gamma ray detectors 15*a*, 15*b* in an identical energy range are determined by the synchronous measurement device 19 to be higher than any of predetermined thresholds corresponding to the energy range, analyzes a type of an element contained in the reinforced concrete 3 on the basis of the energy range in question, and detects a location of the analyzed question in the reinforced concrete 3, more specifically a depth d from a surface of the reinforced concrete 3 irradiated with the neutron ray 13*a*, on the basis of a relative position of the reference point 13*b* on the neutron ray 13*a* relative to the reinforced concrete 3 and the respective measurement points 13*c*, 13*d* (the respective gamma ray detectors 15*a*, 15*b*);

are executed.

The series of the steps are repeatedly executed with moving the non-destructive inspection device 1 to change its position.

Meanwhile a position of a layer of the reinforced concrete 3 subject to the elementary analysis (a depth d from a surface thereof) can be changed by properly changing part or all of a distance L from the surface of the reinforced concrete 3 to the reference point 13*b* on the irradiation axis line of the neutron ray 13*a*, an interval r from the reference point 13*b* to the respective measurement points 13*c*, 13*d* (the respective detectors 15*a*, 15*b*), and an incident direction of the gamma ray detectable by the respective detectors 15*a*, 15*b* (a tilt angle θ relative to the irradiation axis line of the neutron ray 13*a*).

Therefore analysis of elements contained in the reinforced concrete 3 throughout the surface direction and the depth direction of the reinforced concrete 3 will be executed as a plurality of cycles of inspection are repeated with changing part or all of the distance L, the interval r, and the tilt angle θ.

In addition, the predetermined threshold in each energy range used in determination by the synchronous measurement device 19 may be, depending on an element subject to inspection of its distribution, set to be one corresponding to an energy spectrum of a prompt gamma ray radiated from a nucleus of the element. In a case where a distribution of iron in the reinforced concrete 3, for example, a predetermined threshold in each energy range of the prompt gamma ray is set to be one corresponding to an energy spectrum of a prompt gamma ray which a nucleus of iron captures a neutron to radiate. In a case where a distribution of chlorine (chloride ion) in the reinforced concrete 3 is to be inspected, on the other hand, a predetermined threshold in each energy range of the prompt gamma ray is set to be one corresponding to an energy spectrum of a prompt gamma ray which a nucleus of chlorine captures a neutron to radiate.

In the non-destructive inspection device 1 of the present embodiment, when chlorine (chloride ion) in the reinforced concrete 3 is subject to inspection, among predetermined thresholds set in the controller 21, only predetermined thresholds in energy ranges where intensities of a prompt gamma ray emitted by a nucleus of chlorine (chloride ion) are set to be slightly lower than its value, and those in other energy ranges are set to be other values (any value close to infinite for example).

Further the controller 21 sets a threshold in each energy range corresponding to iron and then executes the aforementioned cycles throughout the surface direction and the depth direction of the reinforced concrete 3 to analyze a distribution of iron (reinforcing bar) in the reinforced concrete 3.

Further the controller 21 sets a threshold in each energy range corresponding to chlorine (chloride ion) and then executes the aforementioned cycles throughout the surface direction and the depth direction of the reinforced concrete 3 to analyze a distribution of chlorine (chloride ion) in the reinforced concrete 3.

Further, the controller 21 analyzes a state of corrosion (existence or non-existence of corrosion, possibility of corrosion occurrence, expected time of corrosion occurrence or such) on the basis of how the distribution of the iron (reinforcing bar) is close to the distribution of chlorine (chloride ion) in the reinforced concrete 3.

Thus non-destructive inspection of distributions of elements in the inspection subject can be executed by setting thresholds in respective energy ranges, according to elements subject to inspection of these distributions, to be those corresponding to energy spectra of prompt gamma rays radiated from a nucleus of the elements.

As described above, in accordance with the non-destructive inspection device 1 of the present embodiment, as successively changing part of the reinforced concrete 3 irradiated with the neutron ray 13a in its surface direction and depth direction totally, and detecting an energy spectrum specific to an element from a prompt gamma ray emitted along with capture of a neutron by a nucleus of the element in the reinforced concrete 3, existence or non-existence of the element in the reinforced concrete 3 can be analyzed by destructive inspection.

Because an energy range of a neutron subject to resonant absorption is extremely narrow as shown in FIG. 3, a time taken after generation of a resonant neutron until it reaches a region subject to inspection is also limited to an extremely short period. Further a gamma ray is emitted just after a resonant neutron is absorbed into a nucleus subject thereto (chlorine 35 here). Therefore a time required after generation of a resonant neutron and absorption into chlorine until the generated gamma ray reaches a detector is uniquely determined, and therefore such gamma rays reach detectors having a common distance relative to chlorine 35 at the same time. Thus, as synchronous measurement is executed by a plurality of detectors, gamma rays originating in chlorine 35 alone can be extracted and then measurement accuracy can be improved.

Meanwhile, in the respective embodiments as described above, although an example in which the non-destructive inspection device 1, 1A has the mobile pedestal 11 movable on the reinforced concrete 3 as its subject, the mobile pedestal 11 may be omitted. Further, the gamma ray detectors 15a, 15b of the present embodiment may be disposed with a phase shift at 180 degrees around an irradiation axis line of the neutron ray 13a, or may be disposed with a phase shift at other degrees.

Further, the number of points for measurement where gamma ray monitors (gamma ray detectors) are disposed may be two as in the present embodiment, but may be three or more. Even in a case where gamma ray monitors are disposed at three or more measurement points, the respective measurement points come to be disposed at spots having equivalent intervals from a reference point 13b on an irradiation axis line from the neutron ray source 13 to have phase shifts in arbitrary angles around the irradiation axis line of the neutron ray 13a. Moreover, the gamma ray monitors respectively disposed at the respective measurement points come to respectively detect components of gamma rays in directions inclined at mutually equal angles to the irradiation axis line of the neutron ray 13a, which are from a subject body.

Moreover, the non-destructive inspection device 1, 1A may be modified to have a display means for visualizing and displaying locations of specific elements contained in a reinforced concrete 3 as analyzed in a way described above. In this case, there may be some ways of display by the display means. A data indicating an analysis result of a distribution of chlorine in a depth direction from a surface of the reinforced concrete 3 and a direction of travel of the mobile pedestal 11 can be displayed by a form of contour lines corresponding to concentrations of chlorine, or by a form of shades of indication. Constitutions in which analysis results are visualized and displayed on site are helpful for quick grasp of the analysis results on site where non-destructive inspection of the reinforced concrete 3 is executed.

INDUSTRIAL APPLICABILITY

A non-destructive inspection method without constraints about a shape of a subject body and locations of contained substances, and a non-destructive inspection device preferably applicable to the method, are provided.

The invention claimed is:

1. A method of non-destructive inspection of a subject body including one or more elements, comprising the steps of:
   irradiating the subject body with a neutron ray along an axis line passing through a reference point;
   synchronously detecting gamma rays from directions inclined at equal angles to the axis line at a plurality of measurement points disposed to have equivalent intervals radially from the axis line, respectively;
   measuring the detected gamma rays in a plurality of energy ranges;
   determining whether measured values in the respective energy ranges are beyond thresholds;
   determining energy ranges where all the measured values are beyond the thresholds;
   analyzing a type of an element from the determined energy ranges; and
   detecting a location of the analyzed type of the element in the subject body on the basis of the reference point, the respective measurement points, a relative position relative to a surface of the subject body, and the directions.

2. The method of claim 1, wherein a position radiating the neutron ray relative to the subject body is successively changed along the surface of the subject body to execute the respective steps.

3. The method of claim 1, wherein one selected from the group consisting of a distance from the reference point to the subject body along the axis line, a distance from the axis line to the respective measurement points, and the direction of the gamma ray, is successively changed to execute the respective steps.

4. A device of non-destructive inspection of a subject body including one or more elements, comprising:
   a neutron ray source having a reference point and disposed so as to irradiate the neutron ray along an axis line passing through the reference point;
   a plurality of gamma ray monitors configured to respectively detect gamma rays from directions inclined at equal angles to the axis line, the gamma ray monitors being disposed at a plurality of measurement points having equivalent intervals radially from the axis line;
   a plurality of wave height analyzers configured to respectively measure the detected gamma rays in a plurality of energy ranges respectively, the wave height analyzers being respectively electrically connected with the gamma ray monitors;
   a controller configured to determine whether measured values in each energy ranges are beyond thresholds or not, determine an energy range where all of the measured values are beyond the thresholds, analyze a type of an element from the determined energy range, and detect a location of the analyzed type of the element in the subject body on the basis of the reference point, the respective measurement points, a relative position relative to a surface of the subject body, and the directions.

5. The device of claim 4, wherein the respective gamma ray monitors are configured to be capable of changing one selected from the group consisting of a distance from the reference point to the subject body along the axis line, a distance of the respective measurement points from the axis line, and the direction of the gamma ray.

6. The device of claim 4, further comprising:
   a mobile pedestal configured to be movable on the subject body, on the mobile pedestal the neutron ray source and the respective gamma ray monitors are installed.

* * * * *